US00PP09562P

United States Patent [19]

Saville

[11] Patent Number: Plant 9,562

[45] Date of Patent: May 28, 1996

[54] MINIATURE ROSE PLANT NAMED 'SAVAWIST'

[75] Inventor: F. Harmon Saville, Rowley, Mass.

[73] Assignee: Nor'East Miniature Roses, Inc., Rowley, Mass.

[21] Appl. No.: 364,595

[22] Filed: Dec. 27, 1994

[51] Int. Cl.[6] ..... A01H 5/00

[52] U.S. Cl. ..... Plt./7.1

[58] Field of Search ..... Plt./7.1, 10

[56] References Cited

PUBLICATIONS

Nor'East Miniature Roses, Inc., Supplement 1995. 3 pages Nor'East Miniature Roses, Inc., Rowley, MA.

*Primary Examiner*—Howard J. Locker
*Attorney, Agent, or Firm*—Christie, Parker & Hale

[57] ABSTRACT

A new miniature rose with lavender flowers of good form.

1 Drawing Sheet

SUMMARY OF THE INVENTION

The present invention relates to a new and distinct variety of rose plant of the miniature rose class, which was created by me by crossing as seed parent the variety known as 'Savasach', U.S. Plant Pat. No. 5,967, sold under the trademark Sachet, and as pollen parent the variety known as 'Savalife', U.S. Plant Pat. No. 5,482, sold under the trademark Rainbow's End. The varietal denomination of this new rose is 'Savawist'.

The new variety differs from its seed parent, 'Savasach', in that the latter has larger flowers with fewer petals and is more fragrant. The pollen parent, 'Savalife', differs in flower color inasmuch as flowers of the parent are red and yellow bicolor.

Among the novel characteristics possessed by this new variety which distinguishes it from its parents and all other varieties of which I am aware is its attractive lavender flowers of good exhibition form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

Th accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color desription herein refers to plate numbers in the aforementioned color chart.

Parentage:

*Seed parent.*—'Sachet'.

*Pollen parent.*—'Rainbow's End'.

Class: Miniature.

The following observations are made of specimens grown under glass in Essex County, Mass., during the month of July.

FLOWER

Blooming habit: Recurrent.

A. Bud:

(1) *Size.*—Small.

(2) *Form.*—Pointed, ovate.

(3) *Color.*—As sepals divide, bud color is near 70C.

(4) *Sepals.*—Slightly longer than bud, some foliated and some without foliation, near 146A to 146B.

(5) *Peduncle.*—Length — about ⅞ inch. Aspect — straight. Strength — erect. Color — near 146C.

B. Bloom:

(1) *Size.*—Average size when fully expanded — about 1½ inches.

(2) *Borne.*—Singly and several together in small sprays, flower stem up to about 3 inches when borne singly.

(3) *Form.*—High centered at first becoming flat, petals remaining loosely rolled under, some outer petals quill to points, inner petals often with indistinct apices.

(4) *Petalage.*—Number of petals under normal conditions — about 20–24.

(5) Color.—During first two days, inner petals at center of flower near from near 64A or 64B to 187D and may also vary to between 60B and 60C; outer petals near from near 64A or 64B to 187D and may also vary to between 60B and 60C; base of petals at point of attachment near 2D; reverse of petals of somewhat lighter coloration and general tonality from a distance lilac lavender. As bloom ages the color is near 64A–64B, or near 187D. And the general tonality remains lilac lavender, the normal progression of the bloom is to darken before fading to a lighter color.

C. Petals:

(1) *Texture.*—Thick, firm.

(2) *Appearance.*—Inside velvety and outside satiny.

(3) *Form.*—Fan shaped, broad obovate.

(4) *Arrangement.*—Imbricated, regularly arranged, shingle-like.

(5) *Petaloids in center.*—Sometimes 1 or 2 petaloids.

(6) *Persistence.*—Drop off cleanly.

(7) *Fragrance.*—Slight.

(8) *Lasting quality.*—Up to about 10 days on plant before petals fall and up to about 4 days after cutting.

REPRODUCTIVE ORGANS

A. Stamens, filaments and anthers:

*Arrangement and color.*—Regularly arranged around styles.

*Color.*—Near 21B.

B. Pollen:

*Color.*—Near 21A.

C. Styles: Medium length, even.

D. Stigmas:

*Color.*—Near 23D.

E. Hips: None observed.

PLANT

A. Form: Upright.

B. Growth: Vigorous.

*Height attained.*—About 16 to 22 inches.

C. Foliage: Compound 5 to 7 leaflets.

(1) *Size.*—Small.

(2) *Quantity.*—Abundant.

(3) *Color.*—New foliage: Upper side — near 183B. Underside — near 183D. Old foliage: Upper side — near 139A. Underside — near 138B.

(4) *Shape.*—Oval, pointed.

(5) *Texture.*—Upper side is semi-glossy; underside is matte.

(6) *Edge.*—Serrated.

(7) *Serration.*—Serrate, shallow.

(8) *Leaf stem.*—Color — near 137B. Underside — 137D.

(9) *Stipules.*—Short, smooth.

(10) *Resistance to disease.*—Blackspot — average. Mildew — average. Rust — average.

D. Wood:

(1) *New wood.*—Color — near 143A. Bark — smooth.

(2) *Old wood.*—Color — near 146C. Bark — smooth.

E. Thorns:

(1) *Thorns.*—Quantity (main stalk) — average. On laterals from stalk — average. Form — thin, straight to angled slightly downward. Length — short. Color — near 71A. Position — irregular.

(2) *Prickles.*—None on main stalks, few on laterals.

F. Winter hardiness: Needs protection in severe climates.

I claim:

1. A new and distinct variety of rose plant of the miniature rose class, substantially as shown and described.

* * * * *

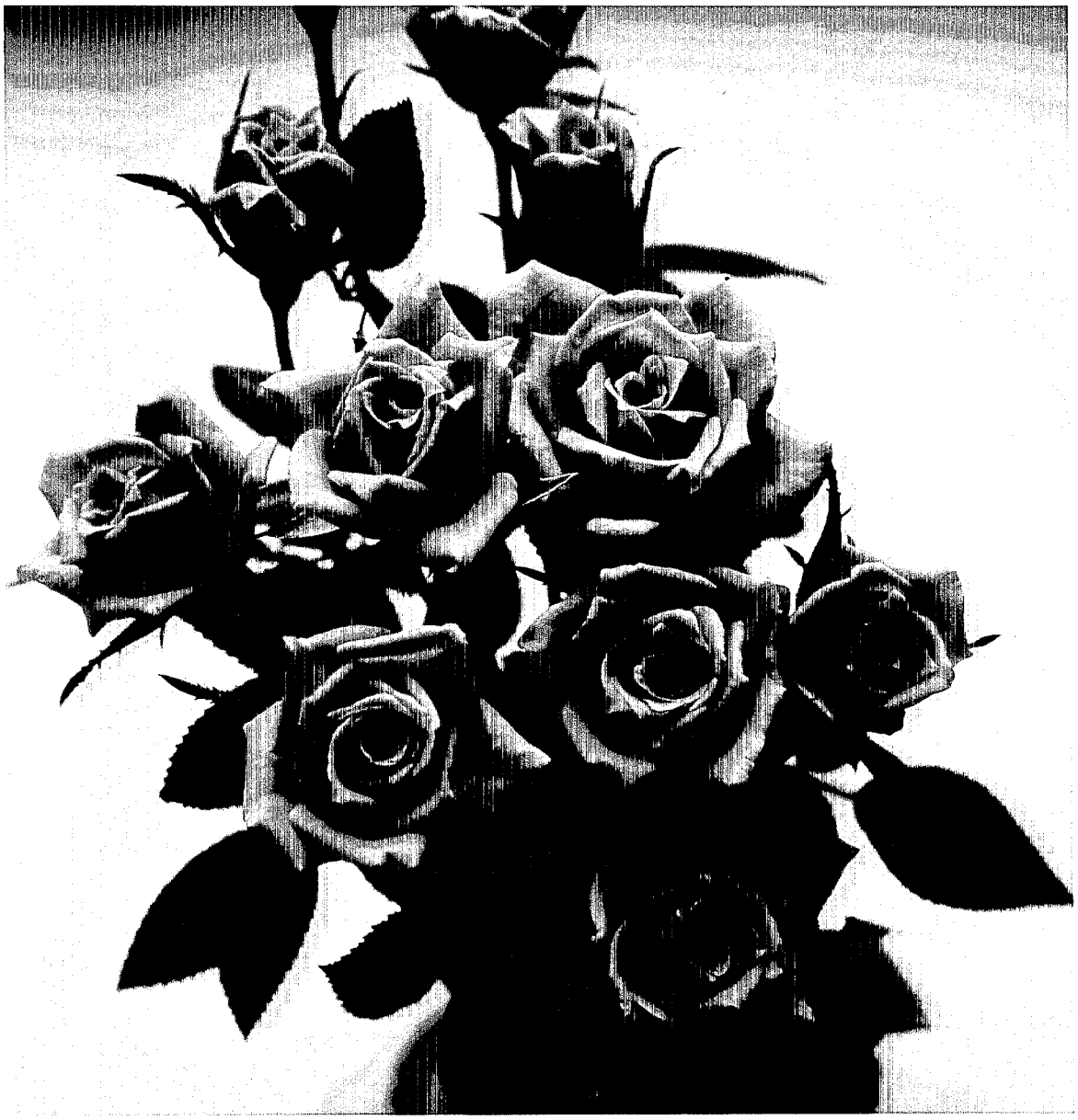

UNITED STATES PATENT AND TRADEMARK OFFICE

CERTIFICATE OF CORRECTION

PATENT NO. : Plant 9,562
DATED : May 28, 1996
INVENTOR(S) : F. Harmon Saville

It is certified that error appears in the above-indentified patent and that said Letters Patent is hereby corrected as shown below:

Column 1, line 6, change "Sachet" to -- SACHET --.
Column 1, line 9, change "Rainbow's End" to -- RAINBOW'S END --.
Column 2, line 19, before "petals" delete "inner".
Column 2, line 19, replace "indistinct" with -- in distinct --.
Column 2, line 24, after "flower" delete "near".
Column 2, line 26, before "from" delete "near".
Column 2, line 30, after "color" replace "is" with -- changes to --.

Signed and Sealed this

Fifteenth Day of April, 1997

*Attest:*

Bruce Lehman

BRUCE LEHMAN

*Attesting Officer*

*Commissioner of Patents and Trademarks*